(12) United States Patent
Schonbrun et al.

(10) Patent No.: US 10,302,559 B2
(45) Date of Patent: May 28, 2019

(54) TOTAL PROTEIN MEASUREMENT USING WHOLE BLOOD REFRACTOMETRY

(71) Applicant: Instrumentation Laboratory Company, Bedford, MA (US)

(72) Inventors: Ethan Schonbrun, Newton, MA (US); Lara Adib, Bedford, MA (US); Gert Blankenstein, Dortmund (DE)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

(21) Appl. No.: 16/211,581

(22) Filed: Dec. 6, 2018

(65) Prior Publication Data

US 2019/0107486 A1    Apr. 11, 2019

Related U.S. Application Data

(62) Division of application No. 15/725,504, filed on Oct. 5, 2017, now Pat. No. 10,168,278.

(Continued)

(51) Int. Cl.
*G01N 21/41* (2006.01)
*G01N 33/49* (2006.01)
(Continued)

(52) U.S. Cl.
CPC ......... *G01N 21/4133* (2013.01); *G01N 21/27* (2013.01); *G01N 33/4915* (2013.01); *G01N 33/6803* (2013.01)

(58) Field of Classification Search
CPC ............... G01N 21/4133; G01N 21/27; G01N 33/6803; G01N 21/553; G01N 21/43;
(Continued)

(56) References Cited

U.S. PATENT DOCUMENTS 5,104,511 A    4/1992  Suzuki et al.
5,331,958 A    7/1994  Oppenheimer
(Continued)

FOREIGN PATENT DOCUMENTS

EP    2793015        10/2014
JP    2009-229196    10/2009
(Continued)

OTHER PUBLICATIONS

Jeanne W. George, "The Usefulness and Limitations of Hand-held Refractometers in Veterinary Laboratory Medicine: An Historical and Technical Review," Veterinary Clinical Pathology, vol. 30, No. 4, 2001, pp. 201-210.
(Continued)

*Primary Examiner* — Hoa Q Pham
(74) *Attorney, Agent, or Firm* — Burns & Levinson, LLP; Joseph P. Quinn

(57) ABSTRACT

An optical system and method for quantifying total protein in whole blood or other multi-phase liquids and colloidal suspensions uses refractometry without preliminary steps such as cell separation or centrifugation. A refractometer is integrated with a flow cell to enable the refractive index of a flowing sample to be measured based on a substantially cell free boundary layer of the sample that is present under certain flow conditions. Dimensions of the flow cell are selected to produce a cell-free layer in a flow of whole blood in which the cell free layer is thick enough to reduce scattering of light from the refractometer light source. A numerical method is used to compensate for scattering artifacts. The numerical compensation method is based on the slope and width of a peak in the derivative curve of an angular spectrum image of the flowing sample produced by refractometry.

13 Claims, 6 Drawing Sheets

Related U.S. Application Data

(60) Provisional application No. 62/407,844, filed on Oct. 13, 2016.

(51) Int. Cl.
    *G01N 33/68*      (2006.01)
    *G01N 21/27*      (2006.01)

(58) Field of Classification Search
    CPC ......... G01N 21/0303; G01N 33/4915; G01N 33/49; G02B 5/008
    USPC ............. 356/128–137, 39–41, 243.1, 243.4
    See application file for complete search history.

(56) References Cited

U.S. PATENT DOCUMENTS

| | | | |
|---|---|---|---|
| 7,280,194 B1* | 10/2007 | Herzinger | G01N 21/4133 |
| | | | 356/128 |
| 7,790,464 B2 | 9/2010 | Tarasev | |
| 9,134,223 B2 | 9/2015 | Garcia et al. | |
| 9,448,166 B1* | 9/2016 | Rainer | G01N 21/4133 |
| 10,168,278 B2* | 1/2019 | Schonbrun | G01N 21/4133 |
| 2014/0262831 A1 | 9/2014 | Balasubramanian et al. | |
| 2015/0025341 A1 | 1/2015 | Sakota et al. | |
| 2015/0033833 A1 | 2/2015 | Bikkina et al. | |
| 2016/0320297 A1* | 11/2016 | Ostermeyer | G01N 21/4133 |
| 2016/0377538 A1 | 12/2016 | Kamrat et al. | |
| 2017/0336385 A1 | 11/2017 | Schonbrun et al. | |

FOREIGN PATENT DOCUMENTS

| | | |
|---|---|---|
| JP | 2010-210384 | 9/2010 |
| JP | 2011232137 | 11/2011 |
| WO | 8801376 | 2/1988 |
| WO | 2009-009081 | 1/2009 |

OTHER PUBLICATIONS

Lien et al., "Rapid Differentiation of Pathogenesis in Patients With Pulmonary Edema by Protein Measurement With Refractometer," Jan. 1, 1995, XP055431187, Retrieved from the Internet: URL:http://ww.ncbi.nlm.nih.gov/pubmed/8605643 [retrieved on Dec. 1, 2017].

International Searching Authority, Invitation to Pay Additional Fees, International Application No. PCT/US2017/055242, dated Dec. 18, 2017, 23 pages.

International Searching Authority, International Search Report and Written Opinion, International Application No. PCT/US2017/055242, dated Feb. 8, 2018, 19 pages.

International Search Report and Written Opinion of Corresponding PCT Application No. PCT/US2017/032613, dated Jul. 17, 2017, 15 pages.

A.Q. Liu, et al.; "Label-free detection with micro optical fluidic systems (MOFS): a review;" vol. 391, No. 7, Anal Bioanal Chem, Feb. 2008, pp. 2443-2452.

Bruls et al., "Rapid integrated biosensor for multiplexed immunoassays based on actuated magnetic nanoparticles," Lab Chip, 9:3504-3510 (2009).

Cattini et al., "A simple measuring system for early detection of haemolysis during haemodialysis," IEEE, 6 pages (2014).

Dong et al., "Accurate in situ measurement of complex refractive index and particle size in intralipidemulsions," Journal of Biomedical Optics, 18(8), 7 pages (2013).

Inline Process Refractometer, MISCO Refractometer, 4 pages, https://www.misco.com/refractometers/inline-process-refractometer ( May 25, 2016).

* cited by examiner

TOTAL PROTEIN MEASUREMENT USING WHOLE BLOOD REFRACTOMETRY

This application is a divisional of co-pending U.S. patent application Ser. No. 15/725,504 filed Oct. 5, 2017, entitled TOTAL PROTEIN MEASUREMENT USING WHOLE BLOOD REFRACTOMETRY, which claims benefit of and priority to U.S. Provisional Patent Application No. 62/407,844 filed Oct. 13, 2016. The entire contents of each of the above applications are incorporated herein in their entirety by reference for all purposes.

FIELD OF TECHNOLOGY

Aspects of the present disclosure are directed to the field of clinical analyzers and more particularly to a method and apparatus for measuring total protein in plasma without separating plasma from a whole blood sample.

BACKGROUND

In a variety of clinical settings, it is important to measure certain chemical characteristics of plasma from whole-blood samples. For example, it is commonly important to measure the analytes, extracellular hemoglobin, bilirubin, and lipid particles in plasma. These settings range from a routine visit of a patient to a physician's office, an emergency room, or monitoring of a hospitalized patient, for example. Numerous techniques and apparatus are commonly used for measuring chemical characteristics of body fluids in clinical settings. Measurement of an analyte in a body fluid sample may be accomplished by numerous methods such as spectroscopic determination and refractometry, for example.

Some techniques for analyzing body fluid are complex and may involve numerous steps such as centrifugation to prepare a fluid sample for measurement. For example, techniques for measuring analyte content in the plasma portion of a blood sample may involve preliminary steps such as centrifugation of whole blood to separate blood cells from the plasma portion. These preliminary steps add time, complexity and cost to previously known techniques for measuring analyte content in a body fluid.

Previous techniques for measuring the total protein content of fluid sample have generally involved measuring optical absorption after addition of a reagent. By contrast, total protein content can also be measured without reagents by quantifying the refractive index of the fluid. The protein content of a substance can be determined based on its refractive index because there is a well-known direct relationship between the refractive index and the protein content.

Refractometry is commonly performed to determine the total protein content of blood plasma by measuring the refractive index of a plasma sample. Previous techniques for using refractometry to measure total protein content in blood involve preliminary steps such as centrifugation to separate cells from the blood. Refractometry is then performed on a sample of the cell free plasma. It has previously been assumed that pure plasma is needed for measuring total protein in blood using refractometry because the presence of blood cells introduces a large light scattering potential which can disrupt the refractometry measurements. Without compensation or optical assess to cell depleted plasma, scattering of light by cells in whole blood significantly reduces the accuracy of a measurement of refractive index.

SUMMARY

Aspects of the present disclosure include an optical method for quantifying total protein in whole blood without preliminary steps such as centrifugation for cell separation. A refractometer is integrated with a flow cell to enable the refractive index of blood plasma to be measured based on a substantially cell free boundary layer of the whole blood sample that is present under certain flow conditions.

When blood flows in a flow path, the thin cell-free layer forms adjacent to a boundary of the flow path fluid. This cell-free layer significantly reduces cell scattering and enables measurement of plasma total protein without preliminary steps of cell separation and without the use of reagents or ultraviolet spectroscopy.

According to an aspect of the present disclosure, dimensions of a flow cell are selected to produce a cell-free layer in a flow of whole blood in which the cell free layer is thick enough to reduce scattering. The effect of scattering by blood cells is not completely eliminated by performing refractometry on the edge layer of a flow cell. However, according to another aspect of the present disclosure, the refractive index of blood with any hematocrit level can be resolved using numerical scattering models. A numerical method is disclosed to compensate for scattering artifacts. The numerical compensation method is based on analysis of the angular spectrum image produced by refractometry.

BRIEF DESCRIPTION OF THE DRAWINGS

The foregoing will be apparent from the following more particular description of example embodiments of the present disclosure, as illustrated in the accompanying drawings in which like reference characters refer to the same parts throughout the different views. The drawings, which are not necessarily to scale, emphasis illustrative embodiments of the present disclosure.

DETAILED DESCRIPTION

Figure 1A:
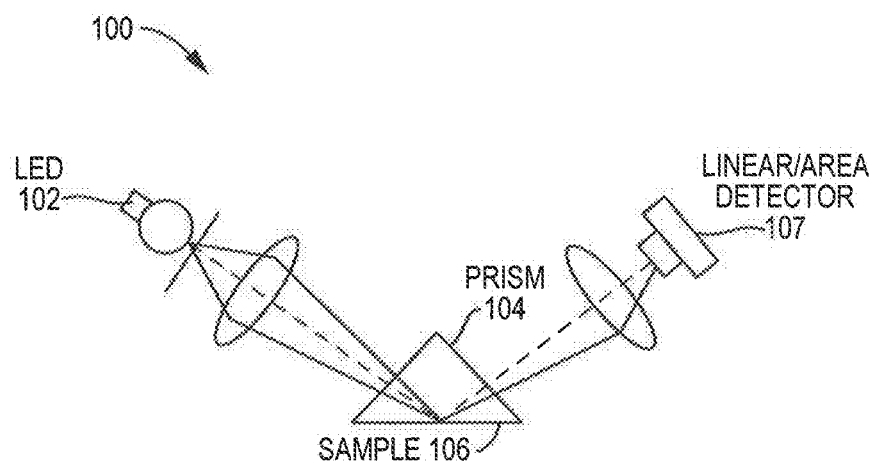
FIGS. 1A-1B are illustrations schematically showing an apparatus for measuring total protein in whole blood without red blood cell separation from the whole blood according to an aspect of the present disclosure.

Aspects of the present disclosure include a method and apparatus for performing refractometry on the substantially cell-free layer of plasma adjacent a channel wall of a channel containing a flowing sample of whole blood. This allows measuring the total protein content in the sample without performing the additional steps of separating plasma from a whole blood sample.

When a whole blood sample flows through a channel having a small cross sectional diameter, such as a blood vessel in the body or a capillary on a chip, for example, the sample behaves as a flow stream in which a substantially cell-free plasma film is present at the edges of the channel. The substantially cell-free plasma film is a very thin layer having a thickness in the range of less than a micron to a few microns at the edge of the channel. It is believed that the substantially cell-free plasma film is present in blood vessels, for example, to help prevent clogging and reduce fluidic resistance of the small blood vessels in the body. The small blood vessels may have cross sectional diameter in a range of about 8 microns, for example.

The disclosed apparatus and method may be implemented to measure the total protein content of a blood sample by analyzing the substantially cell-free plasma film in a flowing sample of whole blood without any need for preliminary separation of plasma from the whole blood sample.

An apparatus for detecting analytes in whole blood without red blood cell separation from the whole blood according to an aspect of the present disclosure includes a channel for receiving a blood sample, and a prism adjacent to the channel. An incoherent light source is directed through the prism with a range of angles of incidence that spans a critical angle relative to a normal of the interface. When whole blood is flowing in the channel, a substantially cell-free plasma layer occupies a thin boundary region of the channel. A light detector is aimed to receive the light from the light source that has been directed through the prism to an optical interface at the boundary of the channel and refracted by the optical interface.

Refractometry techniques disclosed herein involve determining the location of an angular boundary between light that is totally internally reflected and light that propagates into the sample. The position of the boundary is proportional to the refractive index being measured. Scattering of the refracted light by blood cells or other substances in the sample being measured can cause blurring of the boundary and consequently inaccurate measurements of the refractive index.

Scattering of the refracted light during a refractometry measurement also causes the position of the boundary to shift and indicate a smaller refractive index than the true refractive index of a substance being measured.

Aspects of the present disclosure includes a method of reducing the blurring effect of scattering by causing a whole blood sample to flow during a refractometry measurement to generate a substantially cell-free layer in the sample being measured.

Another aspect of the present disclosure includes a method of compensating for the shifting effect of scattering based on the width of a blurry area at the boundary between the area illuminated by refraction and the area not illuminated by refraction.

Certain refractometers provide output by imaging the total internal reflection boundary because the light intensity distribution in the images is based on the refractive index of a substance being measured and resulting angle of refraction. The image is sometimes called the angular spectrum.

FIG. 1A shows and optical schematic of an Abbe refractometer 100 directing incoherent light from a light source such as an LED 102 onto an interface between a prism 104 and a sample 106. The light is directed from a range of angles that spans the critical angel 105 of the sample 106. The critical angle 105 is determined by the index of refraction of the sample and separates light from the light source that is totally internally reflected from light that is not totally internally reflected. The light that is totally internally reflected illuminates a linear area of a light detector 107.

Figure 1B:
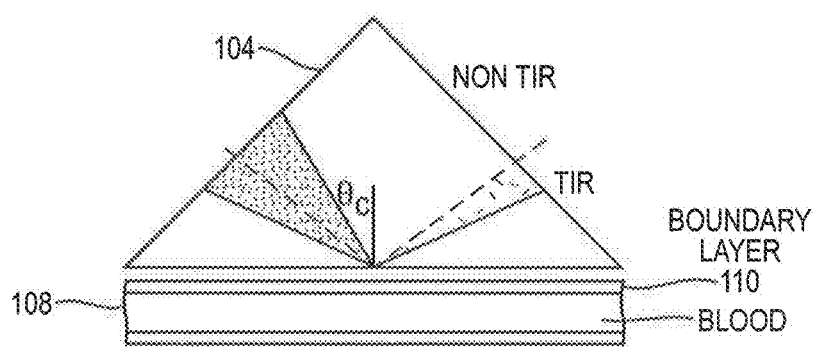

FIG. 1B shows the refractometer 100 integrated with a flow cell 108. The flow cell 108 produces a cell-free layer 110 at an interface between the prism 104 and the flow cell 108 when whole blood 112 flows through the flow cell 108. According to an aspect of the present disclosure, a light source 102 that emits light with a wavelength shorter than green (500 nm) may be used to enable an evanescent decay length that is shorter than the thickness of the cell-free layer 110.

Figure 2:
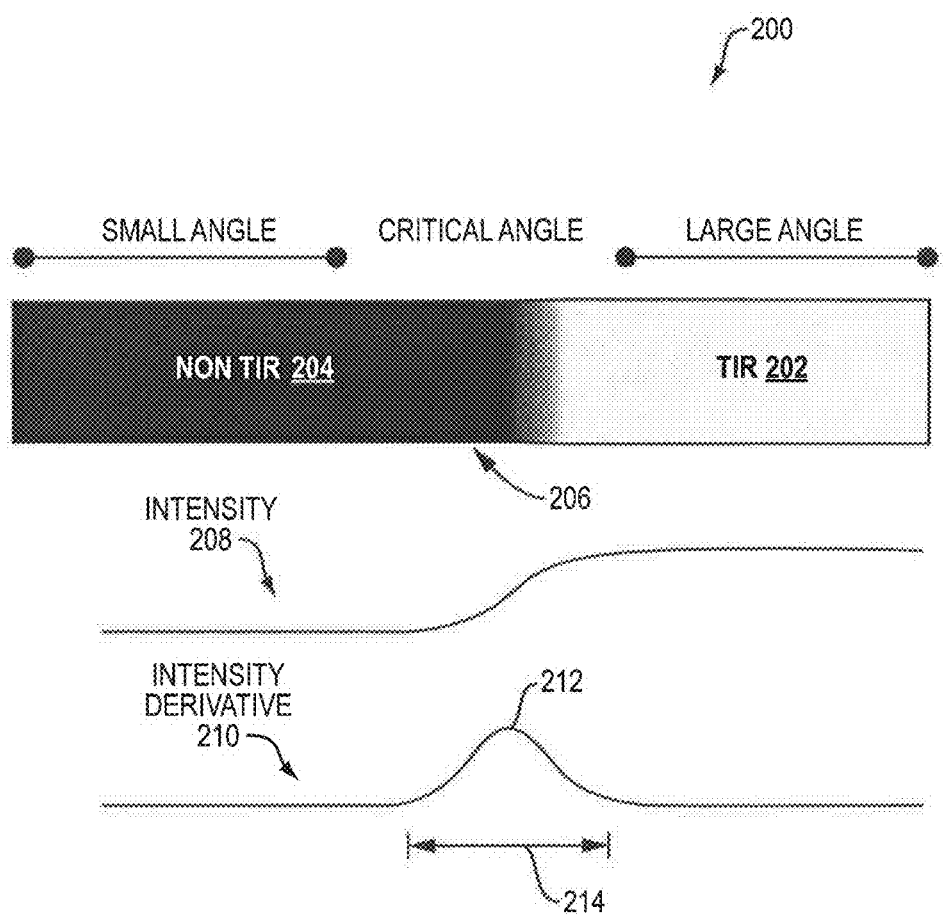
FIG. 2 is an illustration of an angular spectrum image and corresponding intensity and derivative curves according to another aspect of the present disclosure.

FIG. 2 shows an example of an angular spectrum 200 produced by an Abbe refractometer. The angular spectrum 200 is an image of the linear area of the light detector (107, FIG. 1) onto which light from the light source (102, FIG. 1) is reflected. The right side (TIR area 202) of the angular spectrum 200 receives light that has been totally internally reflected from the sample. The left side (non-TIR area 204) of the angular spectrum represents an area that does not receive light that has been totally internally reflected from the sample. A boundary 206 separates the TIR area 202 on the angular spectrum 200 from the non TIR area 204 on the angular spectrum 200. The location of this boundary 206 along the angular spectrum 200 is determined by and indicates the refractive index of the sample.

The boundary 206 can be automatically located by measuring light intensity 208 of pixels along the image of the angular spectrum 200 and numerically determining the location of an intensity change in pixels of the image. For example, an intensity derivative 210 can be computed which indicates the spatial rate of change of light intensity in the image by pixel location, e.g., from left to right. A plot of the intensity derivative vs pixel location numbers provides a peak 212 at the pixel location number corresponding to the boundary position between illuminated areas and non-illuminated areas in the image. The pixel location number of the intensity derivative peak 212 is a direct indicator of the index of refraction of the sample being measured.

The scattering of light by blood cells or other substances in a sample subject to refractometry causes spreading and blurring of the angular spectrum boundary 206. The boundary 206 becomes spread and blurred under scattering but can regain its sharpness under flow. The amount of spreading of the boundary 206 is substantially linearly related to the amount of blood cells or other substance in the sample. The amount of spreading of the angular spectrum boundary also corresponds directly to the width 214 of the intensity derivative curve around its peak 212. According to an aspect of the present disclosure, the width 214 of the intensity derivative curve around its peak 212 can be used as an indicator or the amount of blood cells or other substances in the sample.

The position of the angular spectrum boundary 206 can also shift due to the scattering effect of blood cells or other material in the sample. According to an aspect of the present disclosure, the scattering induced shift of the boundary location toward indicating a smaller refractive index than the true refractive index of a substance being measured can be determined and compensated for based on the width of the intensity derivative curve around its peak. Because the scattering induced shift of the boundary 206 is also directly related to the amount of blood cells or other substances in the sample, the width 214 of the intensity derivative curve around its peak 212 indicates an amount of shift correction that should be applied according to an aspect of the present disclosure to provide a more accurate measurement of refractive index of the sample.

According to an aspect of the present disclosure, a scattering corrected pixel location $P_{corr}$ can be computed using the following equation:

$$P_{corr} = P_m - \chi(\omega - \omega_o)$$ Equation 1;

in which

ω=full width at half maximum of peak of dI(p)/dp where dI(p)/dp=derivative of pixel intensity, and where I($p$)=pixel intensity captured by linear image sensor;

$P_m$=pixel location of peak of dI(p)/dp;

$ω_o$=full width at half maximum of peak for pure plasma (reference width); and

χ is a calibration coefficient.

The calibration coefficient χ depends on characteristic of the refractometer such as prism angle, color, pixel size and lens choice, for example. The corrected pixel location ($P_{corr}$) is proportional to the plasma refractive index, which is proportional to the plasma total protein concentration. In addition to ω, the width of the derivative peak or second moment, other statistical parameters can be used for correction, including higher orders moments such as skew or kurtosis.

Figure 3A:
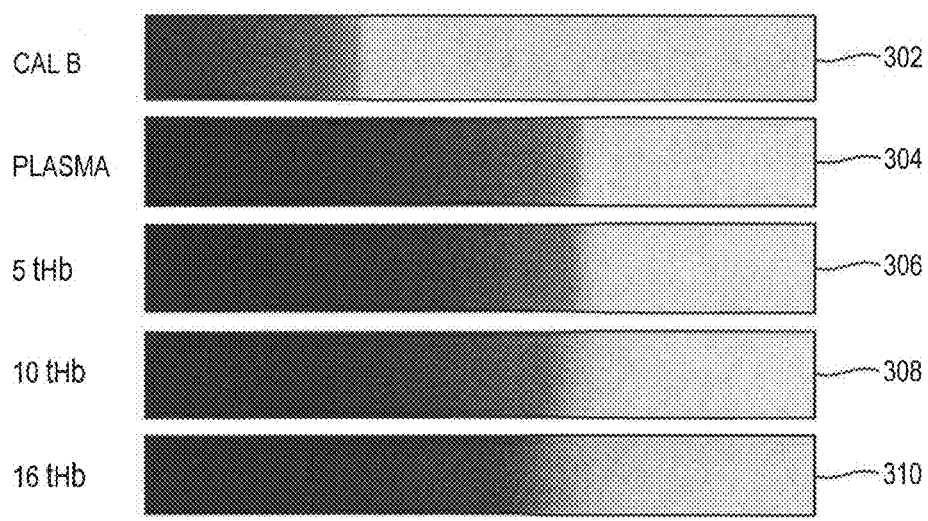
FIGS. 3A-3B are illustrations of angular spectrum images for spectroscopy samples having different levels of scattering and their corresponding derivative curves according to another aspect of the present disclosure.
Figure 3B:
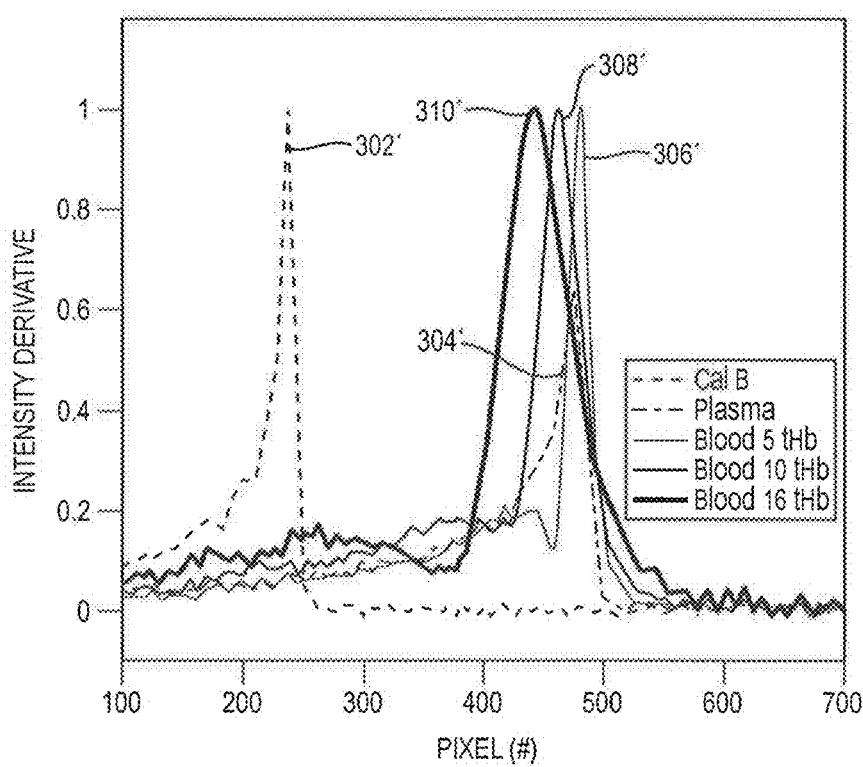

FIGS. 3A-3B shows experimental results of refractometry performed according to an aspect of the present disclosure using blood samples having differing amount of blood cells. The quantity of blood cells in each sample is represented in terms of total hemoglobin (tHb) in units of grams per deciliter. FIG. 3A shows a set of images from a camera of the angular spectrum for five different fluid samples. The first angular spectrum image 302 is a photograph of refracted light from a control sample of Cal B. Cal B is a fluid similar to a saline solution which contains no protein and no hemoglobin. The four remaining images 304, 306, 308, 310 in FIG. 3A are images of the angular spectrum of four samples from the same donor having the same total protein, 7 g/dL, but each has a different quantity of blood cells. The second angular spectrum image 304 is a photograph of refracted light from a sample having 7 g/dL of total protein and no blood cells (0 tHb). The third angular spectrum image 306 is a photograph of refracted light from a sample having 7 g/dL of total protein and tHb of 5 g/dL. The fourth angular spectrum image 308 is a photograph of refracted light from a sample having 7 g/dL of total protein and tHb of 10 g/dL. The fifth angular spectrum image 306 is a photograph of refracted light from a sample having 7 g/dL of total protein and tHb of 16 g/dL.

Even though the four blood samples having angular spectrum images 304, 306, 308, 310 have different blood cell quantities, i.e., different tHb, the images 304, 306, 308, 310 have boundaries between dark and light areas at approximately the same location because the samples they represent have the same total protein content. In this example, the images were acquired while the samples were directed through a flow cell having dimensions of 250 um deep, 5 mm wide at a range of 30 uL/s.

FIG. 3B is a plot of derivative curves 302' 304' 306' 308' 310' of pixel intensity in each of the corresponding angular spectrum images 302 304, 306, 308, 310. The derivative curves 302' 304' 306' 308' 310' represent the spatial derivative direction of pixel intensity versus pixel position in the horizontal direction. Each of the derivate curves 302' 304' 306' 308' 310' has a peak where its slope is maximum. Therefore, the maximum slope of the derivative curve provides an indicator of the angular spectrum boundary location in each image.

According to an aspect of the present disclosure, the width of the derivative peak is used to determine an amount of scattering in order to compensate for the small left shift that exists for high tHb. For example, the angular spectrum image 310 for a sample having 16 tHb includes a boundary that is spread and blurred due to scattering. The boundary location can be more accurately determined by reference to the corresponding derivative curve 310'. Cells in the 16 tHb sample also cause the corresponding derivative curve 310' to shift left, i.e., toward a lower pixel number compared to the derivative peak 304' of the plasma sample having the same total protein content. The amount of shifting is directly related to the amount of blurring by cells in the sample. Blurring of the boundary in the image 310 is also represented as spreading around the peak of the corresponding derivative curve 310'. Therefore determining the width of the derivative curve 310' around its peak can be used to compute a shift compensation factor and a scattering compensated pixel location using equation 1. The scattering compensated pixel location represents a more accurate refractive index of the sample and provides a more accurate measurement of total protein content of the sample.

Figure 4:
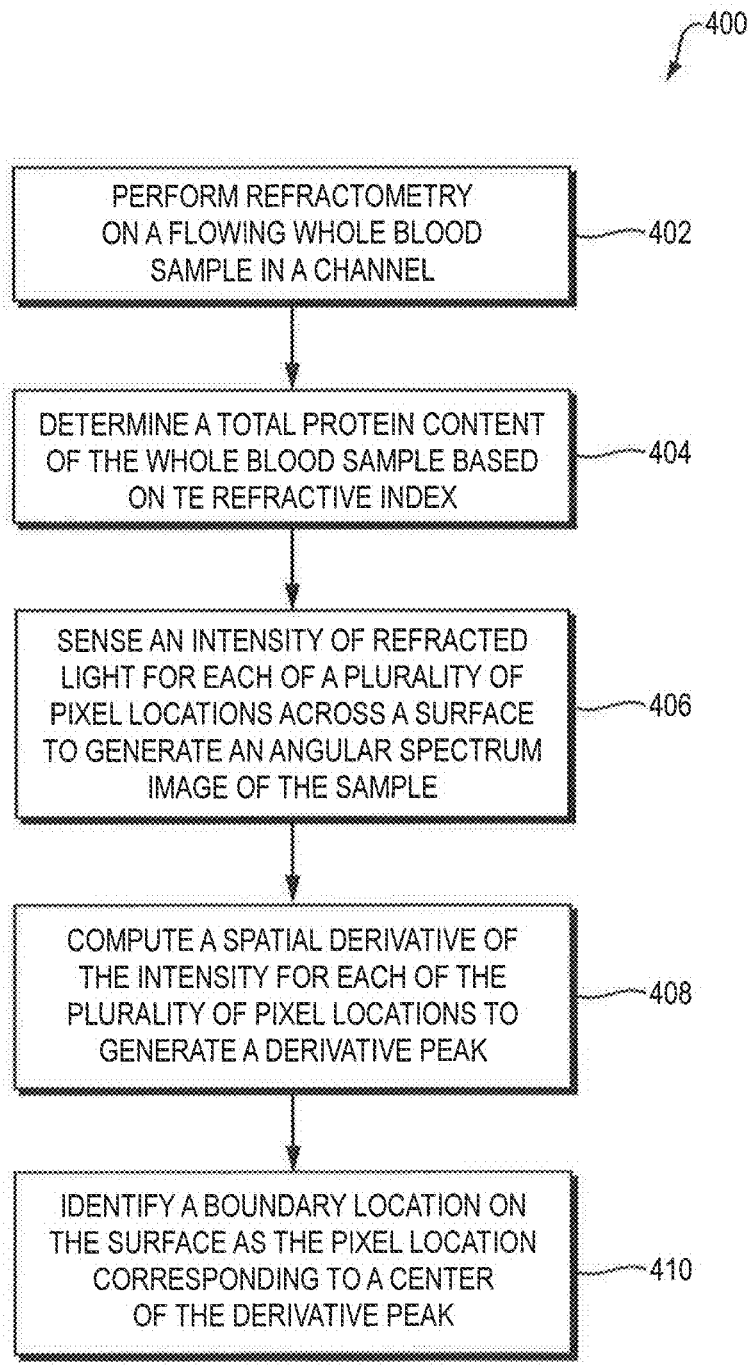
FIG. 4 is a process flow diagram describing a method for measuring total protein in whole blood according to an aspect of the present disclosure.

FIG. 4 is a process flow diagram showing a method 400 for measuring total protein in whole blood according to an aspect of the present disclosure. At block 402, the method includes performing refractometry on a flowing whole blood sample in a channel. In an illustrative embodiment, the channel is about 250 um deep and about 5 mm wide, and the whole blood sample is allowed or caused to flow through the channel at a rate of about 30 uL/s.

The refractometry includes directing a refractometer at a substantially cell free layer of the whole blood sample adjacent a boundary wall of the channel and determining a refractive index of the substantially cell free layer. At block 404, the method includes determining a total protein content of the whole blood sample based on the refractive index. At block 406, the method includes sensing an intensity of refracted light for each of a plurality of pixel locations across a surface to generate an angular spectrum image of the sample. At block 408, the method includes computing a spatial derivative of the intensity for each of the plurality of pixel locations to generate a derivative peak. At block 410, the method includes identifying a boundary location on the surface as the pixel location corresponding to a center of the derivative peak.

According to an aspect of the present disclosure, the method 400 may also include identifying the pixel location corresponding to a center of the derivative peak by identifying a pixel location corresponding to a maximum slope of the derivative peak.

According to another aspect the method may also include computing a correction factor based on a width of the derivative peak, applying the correction factor to the identified boundary location to generate a corrected boundary location and determining the refractive index based on the corrected boundary location.

According to another aspect of the present disclosure, the method 400 may include directing the refractometer at a plasma sample, and sensing an intensity of refracted light from the plasma sample for each of a plurality of pixel locations across a surface to generate an angular spectrum image of the plasma sample. A spatial derivative of the intensity for each of the plurality of pixel locations in the angular spectrum of the plasma sample is computed to generate a reference derivative peak of the plasma. A reference boundary location on the surface is identified as the pixel location corresponding to a center of the reference derivative peak.

According to an aspect of the present disclosure the correction factor is computed by determining a first full width in pixels of the derivative peak at a half maximum height of the derivative peak, determining a second full width in pixels of a reference derivative peak at a half maximum height of the reference derivative peak, and subtracting the second full width from the first full width to generate a width difference. The width difference is then multiplied by a calibration coefficient, which is based on one or more characteristics of the refractometer such as prism angle, color, pixel size and lens type, for example.

Figure 5:
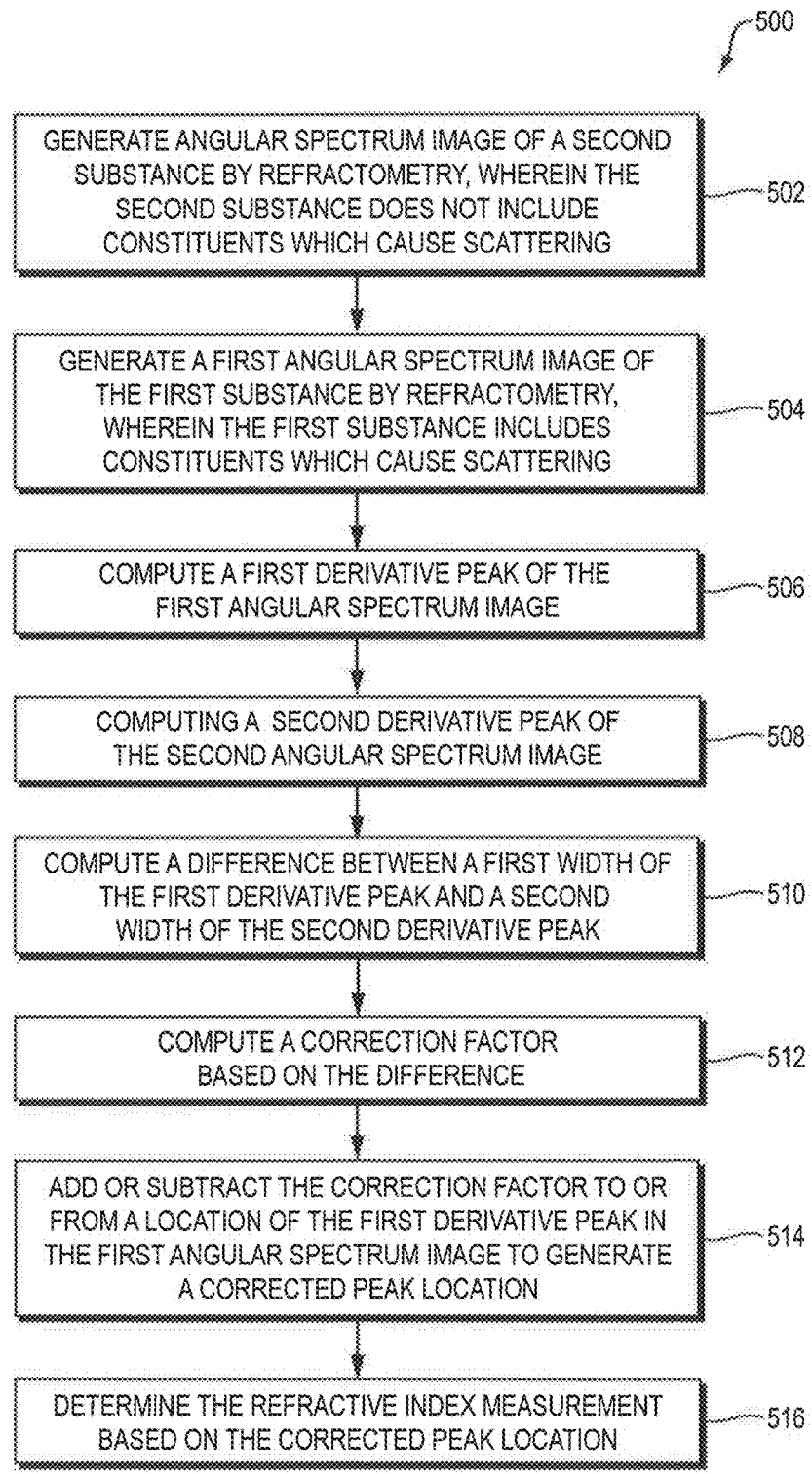
FIG. 5 is a process flow diagram describing a method correcting a refractive index measurement according to an aspect of the present disclosure.

FIG. 5 is a process flow diagram showing a method 500 for correcting a refractive index measurement of a first substance according to an aspect of the present disclosure wherein the first substance includes constituents which cause scattering of light during the refractive index measurement. At block 502, the method includes generating a second angular spectrum image of a second substance by refractometry, wherein the second substance does not include constituents which cause scattering of light during the refractometry. In an illustrative embodiment, first substance may be blood including blood cells, and the second substance may be blood plasma, for example.

At block 504, the method includes generating a first angular spectrum image of the first substance by refractometry. At block 506, the method includes computing a first derivative peak of the first angular spectrum image. At block 508, the method includes computing a second derivative peak of the second angular spectrum image. At block 510, the method includes computing a difference between a first width of the first derivative peak and a second width of the second derivative peak.

At block 512, the method includes computing a correction factor based on the difference. At block 514 the method includes adding or subtracting the correction factor to or from a location of the first derivative peak in the first angular spectrum image to generate a corrected peak location. At block 516, the method includes determining the refractive index measurement based on the corrected peak location. In the illustrative embodiment wherein the first substance is blood including blood cells and the second substance is blood plasma, the method includes measuring total protein in blood based on the refractive image measurement.

According to an aspect of the present disclosure, the step of determining the refractive index in the method 500 includes sensing an intensity of refracted light for each of a plurality of pixel locations across a surface to generate the first angular spectrum image, computing a spatial derivative of the intensity for each of the plurality of pixel locations to generate the first derivative peak, and identifying a boundary location on the surface as the pixel location corresponding to a center of the first derivative peak. According to an aspect of the present disclosure, the location of the first derivative peak can be determined by identifying a pixel location corresponding to a maximum slope of the first derivative peak.

According to an aspect of the present disclosure, in the method 500, the correction factor is computed by determining a first full width in pixels of the first derivative peak at a half maximum height of the first derivative peak, determining a second full width in pixels of the second derivative peak at a half maximum height of the second derivative peak, and subtracting the second full width from the first full width to generate a width difference. The width difference is multiplied by a calibration coefficient, which is based on one or more characteristics of the refractometer such as prism angle, color, pixel size and lens type.

In an illustrative implementation according to an aspect of the present disclosure, the first substance in method 500 may include whole blood flowing in a channel. In this implementation, the method 500 includes performing refractometry on the first substance by directing a refractometer at a substantially cell free layer of the whole blood sample adjacent a boundary wall of the channel. The method 500 then includes determining a refractive index of the substantially cell free layer and determining a total protein content of the whole blood sample based on the refractive index.

Figure 6:
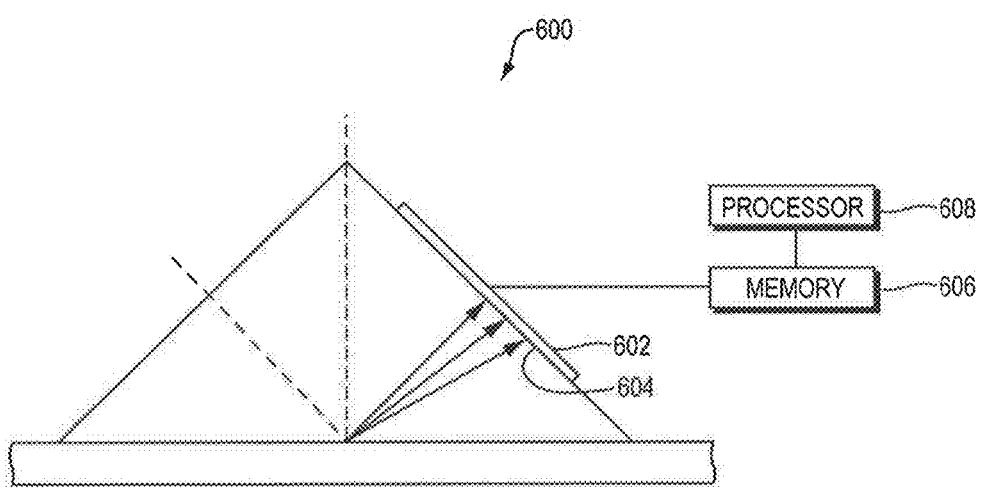
FIG. 6 is an illustration schematically showing an apparatus for measuring a corrected a refractive index according to an aspect of the present disclosure.

An apparatus for measuring a corrected a refractive index of a first substance, which includes constituents that cause scattering of light during the refractive index measurement is described with reference to FIG. 6. The apparatus 600 includes one or more light sensors 602 configured for sensing an intensity of refracted light for each of a plurality of pixel locations across a surface 604 to generate the first angular spectrum image. The apparatus also includes memory 606 coupled to the light sensors 602 for storing the first angular spectrum image. The apparatus also includes processor circuitry 608 coupled to the memory.

According to aspects of the present disclosure, the processor circuitry 608 is configured for computing a spatial derivative of the intensity of each of the plurality of pixel locations to generate the first derivative peak, and for computing a boundary location on the surface as the pixel location corresponding to a center of the first derivative peak. The processor circuitry 608 is also configured for computing a first derivative peak of the first angular spectrum image, computing a difference between a first width of the first derivative peak and a second width of a reference derivative peak, and computing a correction factor based on the difference. The processor 608 is further configured for adding or subtracting the correction factor to or from a location of the first derivative peak in the first angular spectrum image to generate a corrected peak location, and for determining the refractive index measurement based on the corrected peak location.

In an illustrative embodiment, the processor circuitry 608 may be configured for computing a total protein content of the whole blood sample based on the refractive index measurement.

According to another aspect of the present disclosure, the apparatus 600 also includes a channel 610 configured for receiving a flowing whole blood sample. The channel 610 is dimensioned to allow a substantially cell free layer of the flowing whole blood sample to form adjacent a boundary wall of the channel 610. In an illustrative embodiment, the channel is about 250 um deep and about 5 mm wide. The apparatus also includes a light source 612 directed to the substantially cell free layer in the channel 610. The apparatus also includes light sensors configured to receive light from the light source after it reflects and refracts from the substantially cell free layer.

Implementations of the disclosed system and method are not limited to performing refractometry on whole blood samples. According to alternative aspects of the present disclosure, the exclusion region that exists next to the flow cell boundaries when a sample flows through the flow cell can be subject to refractometry to measure the refractive index, and consequently protein concentration, of other multi-phase liquids and colloidal suspensions, for example Although aspects of the present disclosure are described herein in the context of measuring total protein content in whole blood, it should be understood by persons skilled in the art that aspects of the present disclosure can be implemented for detecting various analytes and other constituents in a plasma fraction of body fluid sample.

Although aspects of the present disclosure include methods of compensating for turbidity of a sample when performing refractometry of the sample by computing a spatial derivative of intensity for pixel locations and identifying a boundary location based on a peak of the spatial derivative, it should be understood that various other methods of compensating for turbidity or scattering of light during refractometry are known and can be performed according to other aspects of the present disclosure in addition to or instead of the spatial derivative methodology described herein.

What is claimed is:

1. A method for correcting a refractive index measurement of a first substance, the first substance having constituents which cause scattering of light during the refractive index measurement, the method comprising:
generating a second angular spectrum image of a second substance by refractometry, the second substance not having constituents which cause scattering of light during the refractometry;
generating a first angular spectrum image of the first substance by refractometry;
computing a first derivative peak of the first angular spectrum image;
computing a second derivative peak of the second angular spectrum image;
computing a difference between a first width of the first derivative peak and a second width of the second derivative peak;
computing a correction factor based on the difference;
adding/subtracting the correction factor to/from a location of the first derivative peak in the first angular spectrum image to generate a corrected peak location; and
determining the refractive index measurement based on the corrected peak location.

2. The method of claim 1, wherein determining the refractive index comprises:
sensing an intensity of refracted light for each of a plurality of pixel locations across a surface to generate the first angular spectrum image;
computing a spatial derivative of the intensity for each of the plurality of pixel locations to generate the first derivative peak; and
identifying a boundary location on the surface as the pixel location corresponding to a center of the first derivative peak.

3. The method of claim 1, comprising:
identifying the location of the first derivative peak by identifying a pixel location corresponding to a maximum slope of the first derivative peak.

4. The method of claim 1, comprising:
computing the correction factor by
determining a first full width in pixels of the first derivative peak at a half maximum height of the first derivative peak;
determining a second full width in pixels of the second derivative peak at a half maximum height of the second derivative peak; and
subtracting the second full width from the first full width to generate a width difference.

5. The method of claim 1 comprising:
multiplying the width difference by a calibration coefficient, wherein the calibration coefficient is based on one or more characteristics of the refractometer.

6. The method of claim 5 wherein the characteristics of the refractometer are in the group consisting of prism angle, color, pixel size and lens type.

7. The method of claim 1, wherein the first substance is blood including blood cells, wherein and the second substance is blood plasma.

8. The method of claim 1, comprising:
measuring total protein in whole blood based on the refractive image measurement.

9. The method of claim 1, wherein the first substance comprises whole blood flowing in a channel, the method comprising:
performing refractometry on the first substance, the refractometry comprising directing a refractometer at a substantially cell free layer of the whole blood sample adjacent a boundary wall of the channel and determining a refractive index of the substantially cell free layer; and
determining a total protein content of the whole blood sample based on the refractive index.

10. An apparatus for measuring a corrected a refractive index of a first substance, the first substance having constituents which cause scattering of light during the refractive index measurement, the apparatus comprising:
one or more light sensors configured for sensing an intensity of refracted light for each of a plurality of pixel locations across a surface to generate the first angular spectrum image;
memory coupled to the light sensors for storing the first angular spectrum image; and
processor circuitry coupled to the memory, the processor circuitry configured for:
computing a spatial derivative of the intensity of each of the plurality of pixel locations to generate the first derivative peak;
computing a boundary location on the surface as the pixel location corresponding to a center of the first derivative peak;
computing a first derivative peak of the first angular spectrum image;
computing a difference between a first width of the first derivative peak and a second width of a reference derivative peak;
computing a correction factor based on the difference;
adding/subtracting the correction factor to/from a location of the first derivative peak in the first angular spectrum image to generate a corrected peak location; and
determining the refractive index measurement based on the corrected peak location.

11. The method of claim 10, wherein the processor circuitry is configured for computing a total protein content of the whole blood sample based on the refractive index measurement.

12. The apparatus of claim 10, further comprising:
a channel configured for receiving a flowing whole blood sample and dimensioned to allow a substantially cell free layer of the flowing whole blood sample to form adjacent a boundary wall of the channel; and
a light source directed to the substantially cell free layer, wherein the light sensors receive light from the light source after it reflects and refracts from the substantially cell free layer.

13. The method of claim 12 wherein the channel is about 250 um deep and about 5 mm wide.

* * * * *